United States Patent
Tisci et al.

(10) Patent No.: US 9,586,027 B2
(45) Date of Patent: Mar. 7, 2017

(54) RETRACTABLE NEEDLE CATHETER INSERTION DEVICE

(71) Applicant: Medline Industries, Inc., Mundelein, IL (US)

(72) Inventors: Dante A. Tisci, Hawthorn Woods, IL (US); David S. Noskowicz, Spring Grove, IL (US)

(73) Assignee: Medline Industries, Inc., Mundelein, IL (US)

( * ) Notice: Subject to any disclaimer, the term of this patent is extended or adjusted under 35 U.S.C. 154(b) by 13 days.

(21) Appl. No.: 13/889,063

(22) Filed: May 7, 2013

(65) Prior Publication Data

US 2014/0336582 A1    Nov. 13, 2014

(51) Int. Cl.
*A61M 25/06*    (2006.01)
*A61M 5/32*    (2006.01)

(52) U.S. Cl.
CPC ...... *A61M 25/0631* (2013.01); *A61M 5/3257* (2013.01); *A61M 25/0606* (2013.01);
(Continued)

(58) Field of Classification Search
CPC .......... A61M 25/0631; A61M 25/0693; A61M 25/3232; A61M 25/3234; A61M 25/3243;
(Continued)

(56) References Cited

U.S. PATENT DOCUMENTS

| 4,747,831 A * | 5/1988 | Kulli | A61M 5/322 604/110 |
| 5,395,337 A * | 3/1995 | Clemens | A61M 5/3232 604/110 |

(Continued)

OTHER PUBLICATIONS

Notification of Transmittal of the International Search Report and the Written Opinion of the International Searching Authority, or the Declaration; International Application No. PCT/US2014/034581, Medline Industries, Inc. (Tisci, et al), Aug. 6, 2014.

*Primary Examiner* — Bhisma Mehta
*Assistant Examiner* — Jenna Zhang
(74) *Attorney, Agent, or Firm* — Laubscher, Spendlove & Laubscher, P.C.

(57) ABSTRACT

A retractable needle catheter insertion device is provided with a cannula and a needle positioned within the cannula to assist with insertion of the cannula. After insertion of the cannula into a patient, the needle can retract into a protective sleeve that contains the needle in order to reduce the chance that a medical practitioner will be inadvertently stuck by a used needle. The needle is carried by a needle support that is slidably disposed within the sleeve. A spring biases the needle support and needle toward a retracted position, and the device also includes an activation hub that works in conjunction with the needle support to control retraction of the needle. The retraction may be activated manually by the medical practitioner or may be activated automatically. A modular system and method of manufacturing is also provided in which catheters having either manually or automatic retraction can be manufactured using common parts.

18 Claims, 9 Drawing Sheets

(52) U.S. Cl.
CPC ......... *A61M 5/326* (2013.01); *A61M 25/0618* (2013.01); *A61M 25/0693* (2013.01)

(58) Field of Classification Search
CPC .............. A61M 2005/3235–2005/3239; A61M 25/0612; A61M 25/0618; A61M 25/0625; A61M 25/063; A61M 2005/3223; A61M 2005/3247; A61M 2005/32531; A61M 25/0606
USPC ............................... 604/164.08, 198, 164.12
See application file for complete search history.

(56) References Cited

U.S. PATENT DOCUMENTS

| | | | |
|---|---|---|---|
| 5,501,675 A | 3/1996 | Erskine | |
| 5,562,634 A | 10/1996 | Flumene et al. | |
| 5,573,510 A | 11/1996 | Isaacson | |
| 5,575,777 A | 11/1996 | Cover et al. | |
| 5,676,658 A | 10/1997 | Erskine | |
| 5,685,855 A | 11/1997 | Erskine | |
| 5,690,619 A | 11/1997 | Erskine | |
| 5,700,250 A | 12/1997 | Erskine | |
| 5,702,367 A | 12/1997 | Cover et al. | |
| 5,795,339 A | 8/1998 | Erskine | |
| 5,797,880 A | 8/1998 | Erskine | |
| 5,817,058 A | 10/1998 | Shaw | |
| 5,824,001 A | 10/1998 | Erskine | |
| 5,830,190 A | 11/1998 | Howell | |
| 5,865,806 A | 2/1999 | Howell | |
| 5,911,705 A | 6/1999 | Howell | |
| 5,989,220 A | 11/1999 | Duesman et al. | |
| 6,015,438 A * | 1/2000 | Shaw | A61M 5/3234 604/110 |
| 6,056,726 A | 5/2000 | Isaacson | |
| 6,077,244 A | 6/2000 | Botich et al. | |
| 6,090,078 A * | 7/2000 | Erskine | A61M 25/0631 128/919 |
| 6,224,575 B1 | 5/2001 | Garvin | |
| 6,379,338 B1 | 4/2002 | Garvin | |
| 6,436,070 B1 | 8/2002 | Botich et al. | |
| 6,547,762 B1 | 4/2003 | Botich et al. | |
| 6,582,402 B1 | 6/2003 | Erskine | |
| 6,620,136 B1 | 9/2003 | Pressly, Sr. et al. | |
| 6,872,193 B2 | 3/2005 | Shaw et al. | |
| 6,942,652 B1 | 9/2005 | Pressly, Sr. et al. | |
| 7,044,935 B2 | 5/2006 | Shue et al. | |
| 7,153,276 B2 | 12/2006 | Barker et al. | |
| 7,255,685 B2 | 8/2007 | Pressly, Sr. et al. | |
| 7,344,516 B2 | 3/2008 | Erskine | |
| 7,524,306 B2 | 4/2009 | Botich et al. | |
| 7,678,080 B2 | 3/2010 | Shue et al. | |
| 7,740,615 B2 | 6/2010 | Shaw et al. | |
| 7,753,887 B2 | 7/2010 | Botich et al. | |
| 7,771,394 B2 | 8/2010 | Shue et al. | |
| 8,048,031 B2 | 11/2011 | Shaw | |
| 8,109,905 B2 | 2/2012 | Saulenas et al. | |
| 8,216,188 B2 | 7/2012 | Millerd et al. | |
| 8,313,459 B2 | 11/2012 | Kiehne | |
| 2010/0063455 A1* | 3/2010 | Moyer | A61M 25/0637 604/198 |
| 2010/0191146 A1* | 7/2010 | Botich | A61M 5/158 600/576 |
| 2013/0079713 A1* | 3/2013 | Ho | A61M 5/3232 604/110 |

* cited by examiner

RETRACTABLE NEEDLE CATHETER INSERTION DEVICE

BACKGROUND

The present invention is directed to a medical device for the insertion of intravenous catheters. More specifically, the present invention relates to a catheter insertion device having a retractable needle and to manufacturing methods for the same.

When a catheter is inserted into a patient for the intravenous delivery of a fluid, a disposable needle passing through the catheter cannula is utilized to make a puncture to permit entry of the tip of the cannula into the patient. The needle is then withdrawn leaving the catheter in place either for a connection to the tube of a fluid delivery system. The catheter may also be capped at the time of insertion for later use. The needle used for inserting the cannula no longer has any utility and may now be contaminated with blood or other body fluid that pose an infection or other risk to medical practitioners. Accordingly, the needle must be disposed of without creating a risk of needle sticks to the medical practitioners inserting a catheter. A danger to clean up and medical waste disposal personnel continues if the used needles are not rendered harmless in some way. Caps or covers that can be mounted over the needle are not a satisfactory solution because they must be put in place and can come loose and expose the used needle. A discussion of the dangers associated with various approaches and uses of cannula insertion products is found in U.S. Pat. No. 4,747,831 to Kullie, which is incorporated herein by reference.

Retractable needle mechanisms have been recognized as a solution to some of the safety and disposal problems created by catheter needles. In such retractable needle mechanisms, a cannula insertion needle projects from forward end of the catheter mechanism. The mechanism includes a handle that the medical practitioner grasps while inserting the catheter. The handle includes a hollow portion or sleeve of sufficient size to enclose the needle. After use to start a cannula, the needle is released from the end of the handle and its sharp end retracted into the handle, beyond reach. Preferably the handle has an aperture big enough for the needle but too small for fingertips. The needle rides in a needle support that slides within the handle. Initially the needle support is secured in the handle against the forward end, with the sharp end of the needle protruding outward through the aperture. After the cannula is in place, a release mechanism is triggered. Once the release mechanism is triggered, a coiled spring drives the needle support rearward to retract the needle into the sleeve of the handle. At the rear end of the handle a stop halts the needle support and needle so that they are safely confined within the handle.

The prior art recognizes two general categories of mechanisms for triggering retraction of the catheter needle. In a first category, a manually releasable latch holds the needle support, and thus the needle, in the extended position. After the cannula is in place, the medical practitioner manually triggers the needle support latch by affirmatively actuating a release trigger. This actuation may include squeezing or rotating stop elements out of engagement with the needle support. For example, U.S. Pat. No. 4,747,831, identified above, discloses a manually triggered retraction mechanism.

The prior art also recognizes a second category of triggering mechanism. In the second category, the mechanism is triggered automatically when the medical practitioner withdraws the needle from the cannula after the cannula has been inserted into the patient. In some examples, the needle support is held in place by a latch mechanism that is biased in place by the cannula hub. As the handle is removed from the cannula hub, the latch mechanism actuates, and the needle is automatically retracted into the handle. U.S. Pat. No. 5,562,634 to Flumene, et. al., which is incorporated herein by reference, discloses an automatically retracting needle.

Both of the manually activated and automatically retracting mechanisms provide advantages and disadvantages. For example, the manually activated retraction mechanism provides the medical practitioner with more control of retraction, allowing for more control over use and positioning of the catheter. Conversely, this mechanism has the disadvantage of requiring a separate action to retract the needle, which may be difficult or potentially dangerous depending on the situation. In contrast, while automatic retraction mechanisms have an advantage of not requiring an additional retraction step, catheter disassembly from the retraction device is not fully under the timing and control of the medical practitioner because retraction results in immediate separation of the device form the cannula assembly.

Depending on the particular situation in which the catheter is being used, or the preferences of medical practitioner, one or the other retraction mechanism may be preferred. However, prior designs have the different retraction systems have differed notably, having significantly different overall designs and components. This approach has required greater design and development work, practitioner training, and, in particular, greater manufacturing time and materials.

Accordingly, a need exists for a retractable needle intravenous catheter that is more readily adaptable to being manufactured and used with either an automatic or manually retracting needle mechanism.

BRIEF DESCRIPTION OF THE DRAWINGS

The foregoing and other advantages of the invention will become apparent upon reading the following detailed description and upon reference to the drawings.

Figure 1:
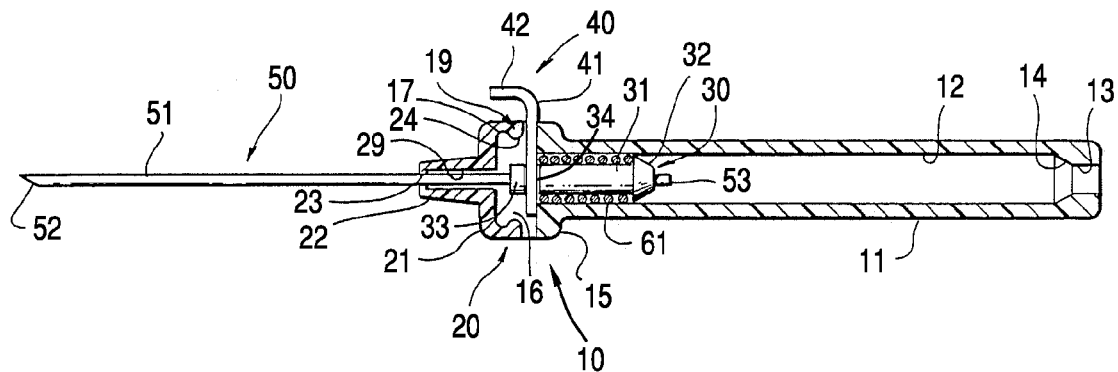
FIG. 1 is a side elevation, mostly in longitudinal section, of an embodiment of the invention, shown with the needle secured in extended position for starting a cannula.

While the invention is susceptible to various modifications and alternative forms, specific embodiments have been shown by way of example in the drawings and will be described in detail herein. It should be understood, however, that the invention is not intended to be limited to the particular forms disclosed. Rather, the invention is to cover all modifications, equivalents, and alternatives falling within the spirit and scope of the invention.

DESCRIPTION OF ILLUSTRATIVE EMBODIMENTS

Embodiments of the invention are now described in detail. Referring to the drawings, like numbers indicate like parts throughout the views. As used in the description herein and throughout the claims, the following terms take the meanings explicitly associated herein, unless the context clearly dictates otherwise: the meaning of "a," "an," and "the" includes plural reference, the meaning of "in" includes "in" and "on." Relational terms such as first and second, top and bottom, and the like may be used solely to distinguish one entity or action from another entity or action without necessarily requiring or implying any actual such relationship or order between such entities or actions. Also, reference designators shown herein in parenthesis indicate components shown in a figure other than the one in discussion. For example, talking about a device (10) while discussing FIG. A would refer to an element, 10, shown in figure other than FIG. A.

Figure 2:
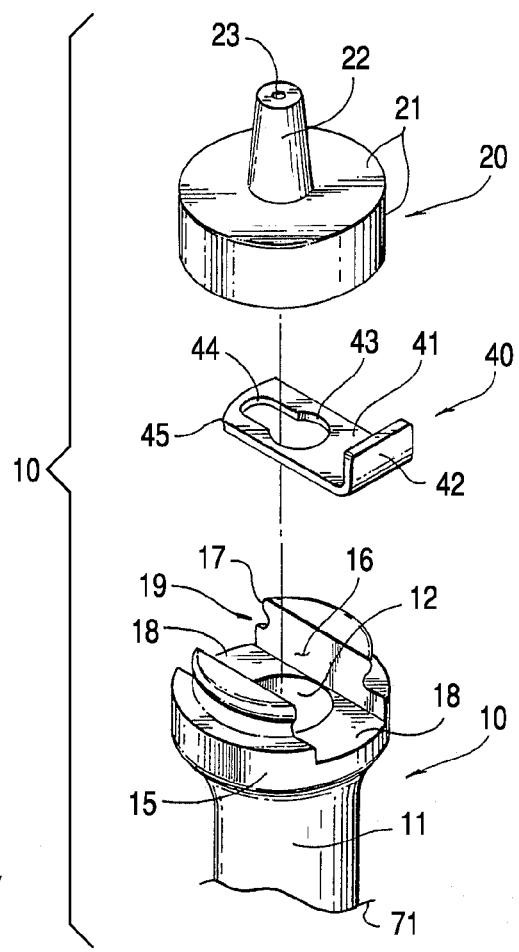
FIG. 2 is an enlarged and exploded perspective drawing, drawn interrupted at one end, of some of the parts of the FIG. 1 embodiment.

As shown in FIGS. 1 and 2, an embodiment includes a retractable needle mechanism that is manually actuated. The embodiment includes an activation hub 10 that is secured to the forward end of a sleeve 11. The activation hub also includes a nosepiece 20 that is securely fixed to a forward end of the activation hub 10. The embodiment further includes a needle support 30 that is slidably disposed within the sleeve 11.

The embodiment of FIGS. 1 and 2 also includes a latch 40 that secures the needle support 30 to the activation hub 10 and a needle 50 that is carried by the support 30 and extends from the activation hub 10 through the nosepiece 20. Finally, this embodiment includes a spring 61 that is positioned within the activation hub 10 and sleeve 11 and that encircles part of the needle support.

The sleeve 11 is preferably but not necessarily injection molded from plastic such as polycarbonate. It includes a long, generally cylindrical outer grip surface, connected at its forward end to a thumb stop 15. The thumb stop is the rearward part of the activation hub 10, shown in FIG. 2. The thumb stop 15 is generally cylindrical, shorter than but coaxial with the sleeve 11.

The remainder of the activation hub 10 is also circularly symmetrical, except that it is bisected at its forward end by a broad transverse latch-guide slot 16, 18. The transverse latch-guide slot 16, 18 has a bottom surface 18 and two opposed side walls 16. As viewed from the end of the device, each side wall 16 of the latch-guide slot 16, 18 is formed along a chord of the circular shape of the thumb stop 15. Thus in effect the latch-guide slot 16, 18 divides the forward portion of the hub 10 into two identical upstanding pillars as seen clearly in FIG. 2. Each pillar is formed as a segment on the chord.

A circumferential groove 19, also better seen in FIG. 2, is formed near the forward end of the activation hub 10. This groove 19 is spaced away from the bottom surface 18 of the latch-guide slot 16, 18. At the very end of the latch housing there is a flange 17, of diameter smaller than that of the thumb stop 15.

A centered longitudinal bore 12 is formed within the sleeve 11. The bore 12 continues through the thumb stop 15 and is exposed at the bottom surface 18 of the latch-guide slot 16, 18. This bore is very generally cylindrical, but may have a very slight taper or draft widening toward the rear end of the handle to facilitate removal of the sleeve and thumb stop from a mold. Near the rear end of the bore 12, however, there is formed an internally frustoconical stop surface 14-narrowing the bore 12 slightly. At the extreme end of the bore 12 is a short end section 13, opening at the rear end of the sleeve 11.

The end section 13 of the bore may be slightly tapered outward toward the rear, and (notwithstanding the drawing) of the same length and taper as the needle guide 22. The taper of the frustoconical stop surface 14 is slight, and the overall diametral inset from the long section 12 of the bore to the end section 13 of the bore is very slight.

The nosepiece 20 forms a forward portion of the activation hub 10 and is a symmetrical article with two sections: a relatively slender forward needle guide 22 and a radially enlarged rearward canopy 21. The needle guide 22 has a central bore that is somewhat larger than the diameter of the needle 50. At the extreme tip of the needle guide 22 this central bore narrows to a fine aperture 23. The diameter of the end aperture 23 is chosen as a tradeoff between (i) complete stabilization of the needle and (ii) minimum friction in sliding clearance between the guide 22 and needle.

The canopy 21 has a generally cylindrical outer surface, preferably matching the outer surface of the thumb stop 15. Formed in the rear end of the canopy is a cavity, internally shaped to mate securely with the contours of the rearward portion of activation hub 10.

More particularly, at the very end of the cavity there is an inward flange or lip 24 (FIG. 1) that accurately fits into and engages the groove 19 of the activation hub 10. Due to the previously mentioned spacing of the groove 19 away from the bottom surface 18 of the latch-guide slot 16, 18, the inward lip 24 of the nosepiece 20 is similarly spaced from the bottom surface 18. The resulting gap defines a track for operation of the latch 40.

The needle support 30 has a very narrow central bore in which the needle 50 is tightly gripped. The support 30 may be manufactured of thermoplastic or other appropriate material and may be press-fit, shrink-fit, and/or cemented on the needle, or molded in place. The outside of the needle support 30 is generally symmetrical and has an extended barrel 31 that may be cylindrical. At the rear end of the barrel 31 is a frustoconical stop section 32 whose forward end is radially enlarged relative to the barrel 31. The stop section tapers inward toward the extreme rear of the needle support 30.

The rear, frustoconical surface of the stop section 32 is shaped to seat against the previously mentioned internal frustoconical stop section 13 of the sleeve 11, when the needle is fully retracted. The front end of the stop section 32 forms a generally planar, annular, step radially outward from the barrel 31, for purposes to be seen shortly.

The forward end section 33 of the needle support 30 is of the same diameter as the barrel section 31.

Embodiments of the needle support include an engaging element. In this exemplary embodiment the engaging element is a detent or circumferential latch groove 34 formed between the forward end section 33 and the barrel 31. Thus the forward end section 33 forms a flange adjacent to and just forward from the latch groove 34.

The latch 40 has a flat slide section 41, and at one end of the slide a short pushbutton section 42 bent or formed at right angles to the slide 41. A keyhole-shaped cutout 43, 44, is defined in the slide. The enlarged portion 43 of this cutout is nearer to the pushbutton 42. The end 45 of the slide 41 opposite the pushbutton 42 lies immediately past the narrowed portion 44 of the cutout 43, 44. The latch can be made from a suitably selected material, including stainless steel or thermoplastic.

The needle 50, with its shaft 51, sharpened tip 52 and rear end 53, is generally conventional—and may be made of stainless steel. It is sufficiently long to allow for the length required to pass into and through the needle support 30. The support 30 is fixed upon the needle shaft 51 very near the rear end 53 of the needle.

Finally the embodiment illustrated in FIGS. 1 and 2 includes a coil spring 61, sized to encircle the outside diameter of the needle support barrel 31. The spring should be long enough to hold the mechanism fully retracted. The minimum diameter of the handle bore 12 is selected to just enclose the spring 61—without significantly restricting the free expansion of the spring.

To assemble the device, the needle support 30 is first fixed to the needle 50 as previously described. Then the needle 50 is inserted through the spring 61, until the needle support 30 reaches the spring. This same general motion is then continued, to insert the flange 33 and barrel 31 of the needle support through the spring 61. The result of this procedure is that one end of the spring is seated against the previously mentioned step at the rear end of the needle support barrel 31.

Next the needle is inserted into the keyhole cutout 43, 44 in the slide 41, until the needle support 30 reaches the slide 41. The same general motion is continued, passing the flange 33 at the forward end of the needle support through the enlarged section 43 of the keyhole cutout 43, 44 in the slide 41.

The result of this procedure is to align the slide 41 longitudinally with the circumferential groove 34 (between the barrel 31 and flange 33) in the needle support 30. Next the slide 41 is moved laterally toward the pushbutton 42 so that the narrower portion 44 of the keyhole cutout 43, 44 is captured in the circumferential groove in the support 30. The needle support 30, with the needle 50, spring 60 and latch 40 in effect threaded upon it as just described, is then inserted rear-end-first into the front end of the bore 12 in the thumb stop 15 and sleeve 11.

The slide 41 thus fits between the two side walls 16 of the latch-guide slot 16, 18, and rests against the bottom surface 18 of the slot. The needle is then inserted through the bore 29 and clearance aperture 23 in the nosepiece 20; and the shaped forward end 16, 17, 19 of the latch guide is then snapped in place within the canopy 21 of the nosepiece 20.

The activation hub 10 is now in effect longer, by the added length of the nosepiece 20. When assembled in this way, the slide portion 41 of the latch 40 is positioned in the previously mentioned "track" that is defined between the bottom surface 18 (FIG. 2) of the latch-guide slot 16, 18 and the inner lip 19 (FIG. 1) of the nosepiece 22.

The pushbutton 42 is pulled fully outward radially from the activation hub 10. The needle 50 is now firmly secured in position, extending forward from the effectively lengthened handle.

After the nosepiece 20 is snapped into place on the forward end of the activation hub 10, these two parts may be secured together by sonic welding, or by an alternative method such as cement, through pins, etc., to ensure permanence of attachment—and thus permanence of capture of the needle after retraction.

In addition, a safety cover for the needle may be provided to protect against accidental puncture and against contamination of the needle before use. The cover must be adapted to fit over the pushbutton 42 without triggering it—and may also to fit between the pushbutton 42 and the canopy 21, to deter movement of the slide 41 due to vibration in shipment or other handling.

Figure 3:
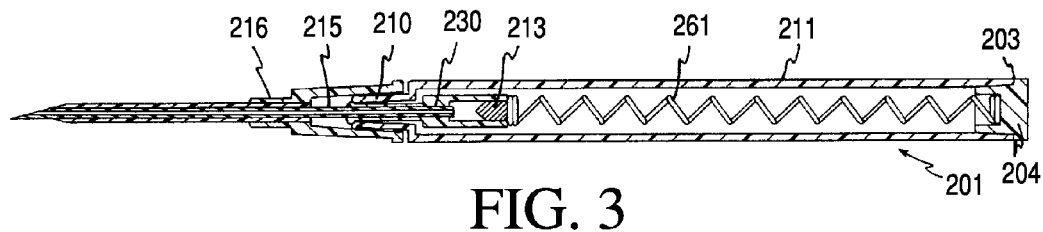
FIG. 3 is a longitudinal sectional view of an embodiment of an intravenous catheter.
Figure 4:
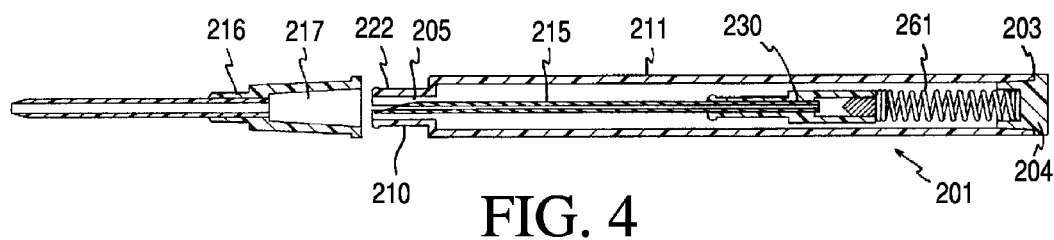
FIG. 4 is a view similar to FIG. 5, taken after the needle has been removed from the cannula.
Figure 5:
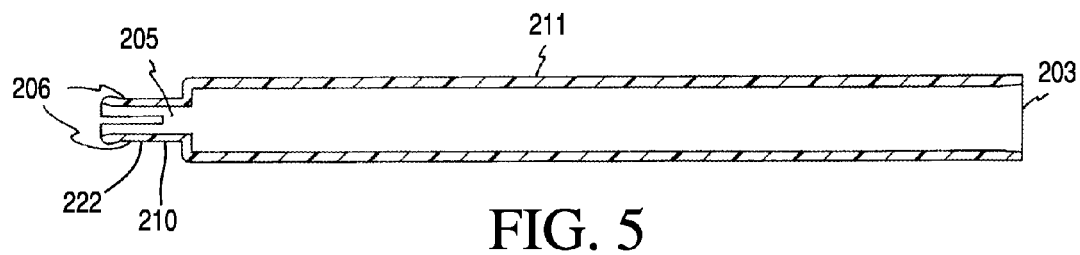
FIG. 5 is an enlarged longitudinal sectional view of the sleeve and activation hub used in an embodiment of a catheter.

In an additional embodiment of the present invention, referring to FIGS. 3-5, an embodiment of a catheter 201 includes a sleeve 211. The sleeve 211 is hollow and has an inside diameter sufficiently great to permit the sliding of needle support 230 and retractor 261 inside of the sheath. The sleeve 211 has an open rear end 203, which is closed by stopper 204. As can be seen in the drawings, the stopper 204 also serves as the anchor for the retractor 261.

Figure 6:
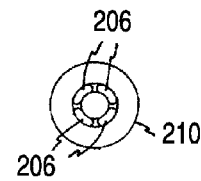
FIG. 6 is an enlarged end view of the activation hub.

The opposite end of the sleeve is also open and is connected to an activation hub 210, which defines an opening 205 having a diameter less than that of the sleeve 211, through which the needle 215 and a portion of the needle support 230 extend prior to removal of the needle from the cannula 216. The activation hub 210 may be secured to the forward end of the sleeve 211 by ultrasonic welding, adhesive, press fit, or any other appropriate method. Alternatively, the activation hub 210 may be integrally formed with the sleeve 211. As illustrated in FIGS. 5-6, it can be seen that the activation hub 210 comprises a plurality of engaging components, which in the illustrated embodiment comprise four resilient arms 206. Each of the engaging components is separated from the adjacent components by a longitudinally-extending gap. In assembly of the catheter, this permits the components 206 to be urged toward each other to define an opening 205 of reduced diameter when the tip 222 of the activation hub 210 is inserted into the frusto-conical cavity 217 of catheter cannula 216. However, since the components 206 are of a resilient construction, the components will return to their original positions when the restraining force is removed.

Figure 7:
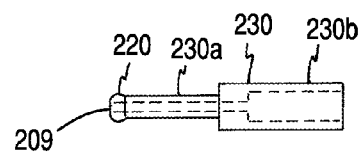
FIG. 7 is a side view of a needle support used in an embodiment of the catheter.
Figure 8:
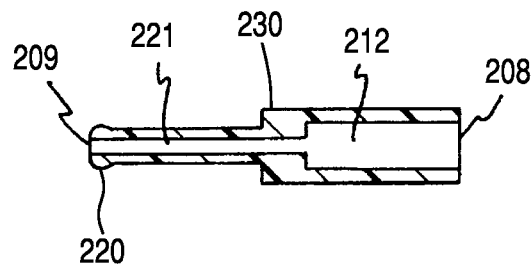
FIG. 8 is an enlarged longitudinal sectional view of the support of FIG. 7.

Needle 215 is carried by needle support 230. As seen in FIGS. 7 and 8, the support 230 includes two coaxial cylindrical portions 230*a* and 230*b*. Portion 230*a* has a diameter small enough to permit it to pass through the opening 205 in the activation hub 210 and through the tip 222. Portion 230*a* is provided with a central cavity 221 into which the needle is inserted. The end 209 of the support is provided with an engaging element, in the illustrated embodiment a lip 220, which is capable of engaging the tip components 206 when the needle is in the cannula. See FIG. 9.

Portion 230*b* has a diameter which is small enough to permit it to move in the sleeve 211, but large enough that it does not pass through the opening 205 in the sheath end. Portion 230*b* is provided with a central cavity 212 which can act as a blood control chamber. The open end 208 of the cavity 212 can be closed with a stopper 213, which is made of a material which can absorb blood, but which permits the passage of air. It is also possible to provide the stopper 213 with a second anchor for the retractor 261.

The retractor 261 may be, for example, a cylindrical spring. Other types of retractors can be used, as long as a continuous withdrawing force is exerted on the support 230. In the case of the illustrated spring, one end is fixed to the support 230, more precisely to the stopper 213 which engages the support in the illustrated embodiment, while the other is fixed to the sleeve 211, more precisely to the stopper 204 which engages the sleeve in the illustrated embodiment. The retractor 261 may be any appropriate biasing element, including a compression spring, an extension spring, an elastomeric string or band, or the like as would be understood by one of ordinary skill in the art.

Figure 9:
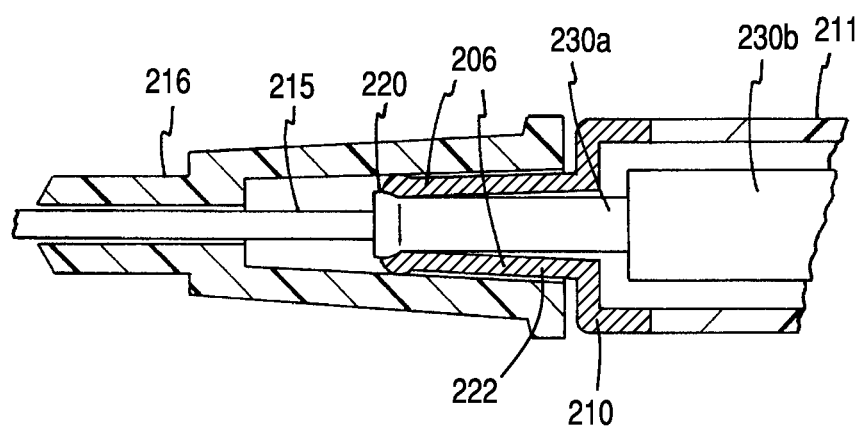
FIGS. 9 and 10 are enlarged longitudinal sectional views of the connection between the sleeve, activation hub and the cannula hub before and after removal of the needle from the cannula.
Figure 10:
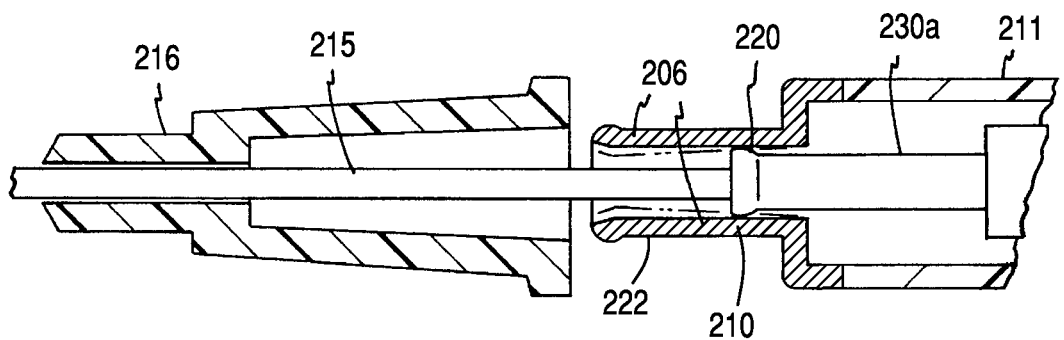

FIG. 9 shows the catheter of this embodiment in the assembled condition, with the tip components 206 of the activation hub 210 in the inwardly compressed or biased position. FIG. 10 shows the catheter as the needle 215 is being removed from the cannula, with the broken lines illustrating the position of the tip components 206 when in the assembled position. Referring to FIGS. 9 and 10, when the catheter of the present invention is assembled, the insertion of the tip 222 into the frusto-conical wall of the cavity 217 of the cannula urges the tip components 206 toward each other. This effectively reduces the size of the opening 205 in the tip and causes the tip 222 to tightly grip the end 209 of the needle support 230. This prevents the retraction of the needle 215 by the retractor 261. Thus, the needle is held in the exposed position. This gripping is facilitated by the provision of lip 220 on the end 209. If desired, a removable auxiliary sheath (not shown) can be provided on the needle or cannula to provide protection while the catheter is handled before use.

After the needle and cannula have been inserted in the blood vessel of the patient, the needle is removed by pulling on the sleeve 211 and or activation hub 210. As the tip 222 is removed from the frusto-conical cavity 217, the resilient tip components 206 move outwardly toward their original positions prior to assembly, thereby effectively increasing the size of the opening 205 in the tip. When the components move sufficiently to define a diameter which is greater than that of the lip 220 of the support end 209, the obstacle to the force applied by the retractor 261 is removed. Thus, this movement of the tip components permits the support 230 to be withdrawn under the force exerted by the retractor, thereby quickly and automatically withdrawing needle 215 to the interior of sleeve 211, as shown in FIG. 6. The force exerted by the retractor 261 will tend to retain the needle within the sleeve 211. The sleeve 211, with the needle 215 inside, can then be discarded. This withdrawing takes place without any voluntary action by the medical practitioner and is a result only of the removal of the activation hub 230 from cannula hub.

Figure 11:
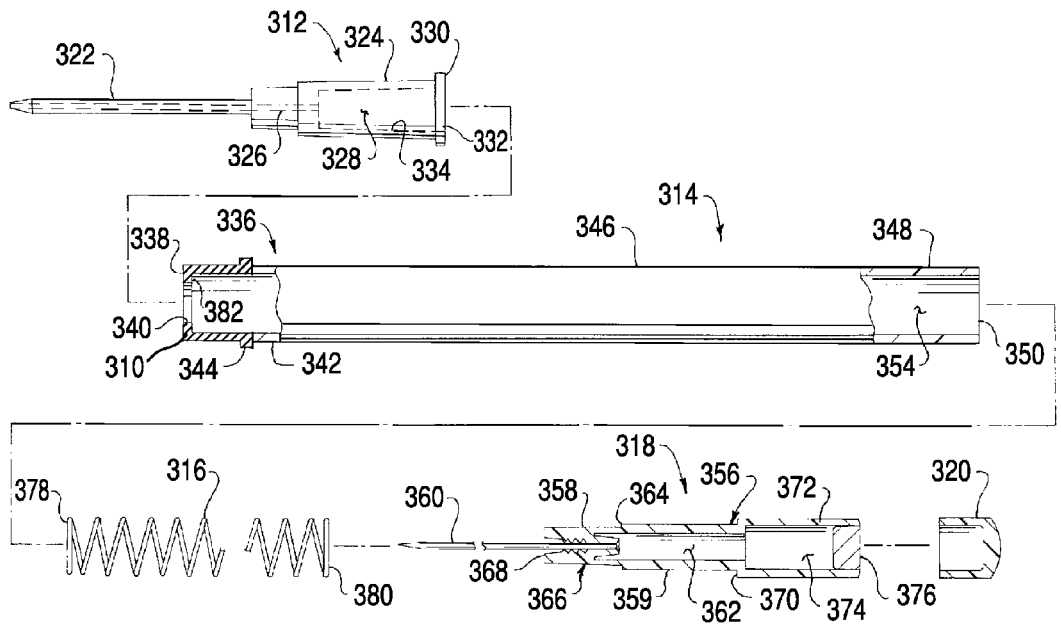
FIG. 11 is an exploded side elevation of a further embodiment.

FIG. 11 shows the exploded assembly of a further embodiment of a retractable needle catheter device with the exception of the common protective cap that is placed over the needle. Parts illustrated include the cannula hub assembly 312, sleeve 314, hub 310, biasing element or spring 316, needle support 318 and closure element 320.

Cannula hub assembly 312 includes a flexible plastic or rubber cannula 322 and a hub 324 having a needle channel 326 and a hollow portion 328 having a flange 330 with an opening 332. Hollow opening 328 has a tapered inner surface 334 comprising a connection surface.

Sleeve 314 has a front end portion 336 that is connected to a hub 310. The hub 310 may be secured to the sleeve by ultrasonic welding, adhesive or other appropriate means. Alternatively, the hub 310 may be integrally formed with the sleeve 314. Sleeve 314 is preferably defined by a continuous wall 342. Sleeve 314 has an intermediate section 346 and a rear end portion 348 having an opening 350 in the rear end portion. Wall 342 defines an inner space or retraction space 354. As is conventional, the body is molded from clear plastic so the operator can see when the catheter is properly inserted in a patient. The hub has a forwardly facing surface 338 and an opening 340 in the front end. The hub may be provided with one or more stops 344 for a conventional protective cap over the needle. Biasing element 316 is preferably a coil spring.

Needle support 318 comprises a retraction body 356 having a front portion 358 carrying a catheter insertion needle 360 which is fixed in place. The internal center of front portion 358 has irregular openings in its center portion to assist in gluing the needle in place. The hollow needle creates a fluid passageway into a chamber 362 immediately behind front portion 358. A step 364 creates a slightly larger diameter in the central body portion of retraction body 356. A connection surface 366 is created along the outside surface of front portion 358 between the front 368 of front portion 358 and step 364. A second step 370 at the back of the intermediate portion of body 356 serves as a spring seat. It denotes the beginning of an enlarged rear portion 372 having an outer surface slightly smaller than the inside diameter of sleeve 314 and encloses a flash chamber 374. Rear portion 372 has an open back end which is tightly fitted with a porous plug 376 for the passage of air displaced by fluid. Spring 316 has a front end 378 and a back end 380 which fits against spring seat 370. Spring 316 fits over reduced diameter intermediate body section 359.

Figure 12:
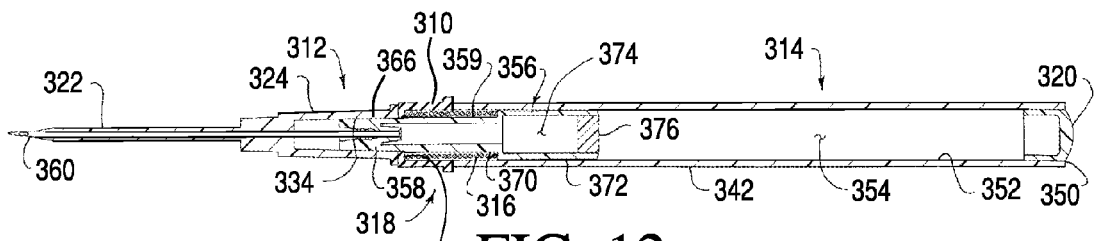
FIG. 12 is a side elevation cut away through the center line of the assembled parts of FIG. 11.

FIG. 12 shows an embodiment of a retractable needle catheter device in its assembled ready-to-use condition. After needle 360 is glued into the front of needle support 318, spring 316 is mounted from the front over intermediate body section 359 of needle support 318 with its back 380 against seat 370. This assembly is inserted from the rear through opening 350 of sleeve 314 and spring 316 is compressed against a ledge 382 formed at the front of the hub 310. The front portion 358 of needle support 318 is then pushed through opening 340 and extended forwardly beyond the front of hub 310. The hollow cannula hub 324 is releasably mounted on the front part of the needle support, preferably in a sliding friction fit between connection surface 366 and inner surface 334, which are mating surfaces. Cannula hub 324 holds needle support 318 in place against the retraction force applied in the retraction direction by the compressed spring. Then a closure element or cap 320 is snugly fitted into opening 350 at the back of sleeve 314 to make sure the retracting parts cannot come out of the sleeve. Rear portion 372 of retraction body 356 is slightly smaller in diameter than the inside diameter of chamber 354 so the retraction body is free to slide in the lineal direction along the length of sleeve 314. Depending on the tightness of the fit, closure 320 may include a vent to permit the escape of trapped air.

Figure 13:
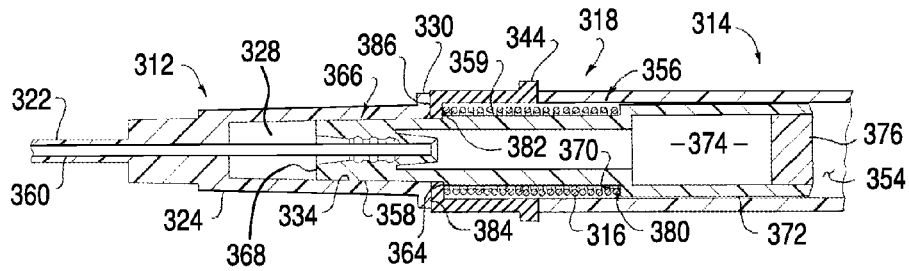
FIG. 13 is a partial enlargement of FIG. 12 showing how the needle support is held in the unretracted position by the cannula hub.

FIG. 13 is an enlarged view which better shows the component parts illustrated in FIG. 12. It is shown in the assembled and ready-to-use position. Here front end (378) of spring 316 is compressed against ledge 382 and back end 380 of spring 316 is compressed against seat 370. Step 364 being slightly wider than opening 340 also fits against ledge 382. It can be seen that the inner surface or connection surface 334 of hub 324 fits tightly over outer surface or connection surface 366 of front portion 358 of retraction body 356. Connection surfaces 334, 366 fit tightly enough together to resist the retraction force applied against retraction body 356 by spring 316. Surfaces 334, 366 are preferably tapered forwardly to smaller diameter to facilitate a friction fit.

Cooperating abutments are provided between the cannula hub and the hub to resist this retraction force. These abutments are provided by means of a rearwardly facing surface 384 of flange 330 of cannula hub 324 and forwardly facing surface 386 on the front end of hub 310. These abutting surfaces come together and cooperate to prevent rearward movement in the retraction direction of cannula hub 324 which thereby restrains retractable body 356. It is noted that front portion 358 of retraction body 356 extends well into hollow hub 324 with the surface 366 in contact with surface 334. As shown, front portion 358 extends about half way into hollow portion 328 of cannula hub assembly 312. This provides for an additional advantage of a desirable stable connection between the two parts which in combination with abutment surfaces 384, 386 avoids any feeling of looseness when the catheter introducer is handled.

Since there is no actual sealing requirement between the cannula hub and the retraction body, which has a completely internal fluid passageway, connection surface 366 does not necessarily need to be a continuous surface. It is contemplated that the one or both of the connection surfaces 334, 366 could be separated lands such as might be visualized running in the longitudinal direction or possibly a series of non-interlocking ridges or fins. It is contemplated that connection surface 366 and inner surface 334 may have complimentary engagement ridges (not shown) in the nature of course threads with a raised profile and a lowered profile on the complimentary part which requires a twist to separate the cannula hub to initiate retraction. In such case it would be desirable to include a means for stopping rotation of the needle support internally of the sleeve. A lateral extension in the vicinity of step 364 and a corresponding stop within sleeve 314 could be applied or the anti-rotation provided by a non-circular shape. Disengagement of the connection surfaces immediately and automatically causes retraction.

Figure 14:
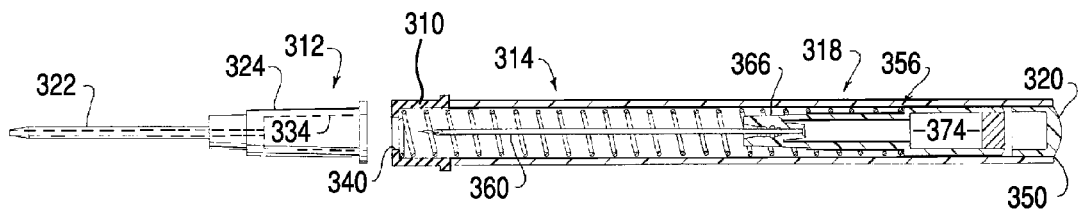
FIG. 14 is a partially cut away side elevation of the automatically retracting catheter introducer of FIGS. 11-13 in the retracted position.
Figure 15:
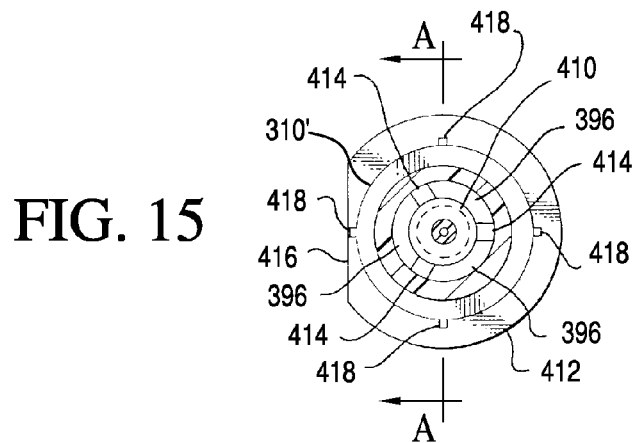
FIG. 15 is a front cross sectional view of a further embodiment on the lines B-B of FIG. 16.

FIG. 14 shows the completely retracted position. Cannula 322 at this point would be inserted into the patient with the cannula hub ready for attachment to a tube for infusion of a fluid while sleeve 314 containing needle support 318 and needle 360 would be discarded. Note that the sleeve 314 is long enough to completely hold the needle support 318 and the entire insertion needle 360. The spring is preferably long enough in its uncompressed state to ensure that the needle support is pushed back far enough into sleeve 314 that needle 360 is not exposed.

An additional embodiment is shown in FIGS. 15-19. The embodiment employs a similar concept as the previous embodiment in that there is immediate self-retraction when the hub is hand separated from the cannula hub, but in this embodiment an activation hub instead of a friction fit with the cannula hub restrains the needle support. The cannula hub does not actually touch the needle support in this embodiment.

Components of this further embodiment are catheter hub assembly 312, activation hub 310', sleeve 314' and needle support 318'. Sleeve 314' has a body portion 388 having a wall 390 with a longitudinally extending tubular inner surface 392 and an opening 350' in back. Closure 320 stops opening 350' after needle support 318' is installed into the sleeve 314' from the rear. Activation hub 310' front portion 394 comprising a plurality of arms 396 surrounding a passageway 398 leading through hub 310' into sleeve 314'. Passageway 398 is occupied by the forwardly extending portion 358' of the needle support to be described. Wall 391 of activation hub 310' is turned inwardly to form the ledge 382' where arms 396 begin. Arms 396 are elongated forwardly from ledge 382' and terminate in protrusions 400. Arms 396 have an arcuate outward surface 402 running from the front surface 386' of activation hub 310' to protrusions 400. The arms have an arcuate inner surface 404 from which protrusions 400 extend inwardly toward the center line. The parts shown are symmetrical.

Needle support 318' comprises retraction body 356' having a flash chamber 374' with a porous plug 376. Retraction body 356' has a rear portion 372' nearly as large in diameter as space 354 within sleeve 314'. Body 356' further includes a stepped down in diameter intermediate portion 359', beginning at step 370. Spring 316 has its front end 378 positioned behind ledge 382' and its back end 380 positioned in front of step 370 and surrounds intermediate body section 359'. There is a further stepped down in diameter portion 358' beginning at step 406 which comprises front portion 358' extending forwardly through passageway 398 between and within arms 396. Front portion 358' preferably extends beyond protrusions 400 to terminate at front end 368'. Front portion 358' has an arcuate outer surface 408 extending between step 406 and front end 368', which in the preferred embodiment is circular tapering to a smaller diameter from back to front.

The needle support 318' also includes an engaging element. In the illustrated embodiment this is a detent or groove 410 that is recessed into surface 408 at a position along surface 408 to receive protrusions 400 which is the means by which retraction body 356' is held by arms 396 in the assembled for use position of FIG. 16. Irregular openings within front portion 358' receive adhesive to install and fix needle 360 extending forwardly through cannula 322 in fluid communication with flash chamber 374.

Figure 17:
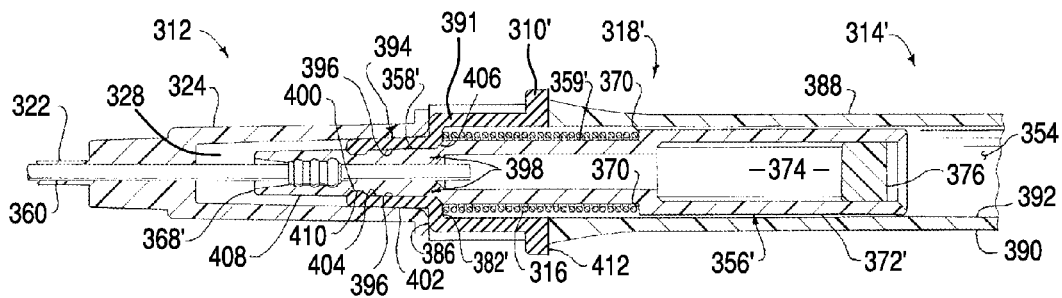
FIG. 17 is a cut away side elevation on the lines A-A of FIG. 15 showing the needle support held in an unretracted position.

Referring now to FIG. 17, a cut away portion of sleeve 314' shows retraction body 356' and compressed spring 316 wherein arms 396 are seen as having the arcuate outer surface 402 being clamped by the open back end portion of cannula hub 324 thereby holding protrusions 400 into groove 410. The inner surface 334 of hub 324 is frictionally held in contact with outer surface 402. Outer surface 402 is preferably tapered to a smaller diameter outwardly like inner surface 334 of hub 324.

Figure 16:
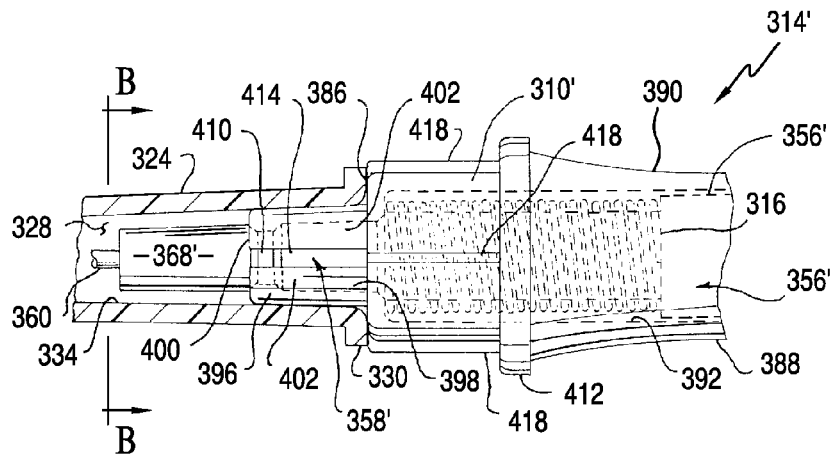
FIG. 16 is a partial cut away side elevation of an embodiment showing all or part of the cannula hub, sleeve, activation hub and needle support.

In FIG. 16, activation hub 310' has a flange 412 wherein three arcuate arms 396 are shown separated by gaps 414. A portion of groove 410 is seen in dotted outline. Flange 412 includes a flat side 416 which conveniently prevents the assembled structure from rolling on a flat surface. Finally, a plurality of longitudinally extending fins 418 serve as support for a protective cap (not shown) which is installed on the front of the tube against flange 412. Front portion 358' extends forwardly through passageway 398 between the arms. The compressed biasing spring is applying a retraction force to the retraction body. Although three arms 396 are illustrated, there could be more or less, so long as they are able to engage and hold the front of the retraction body.

Figure 18:
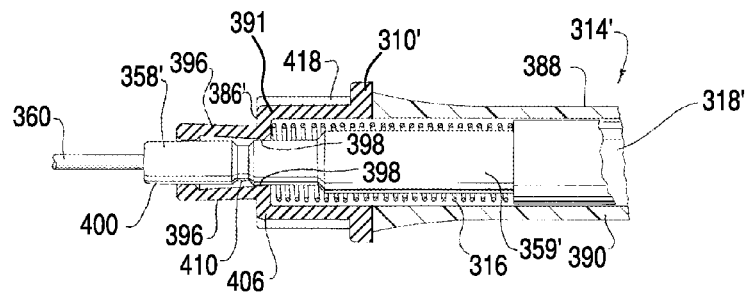
FIG. 18 is a partial cut away view of the working parts of FIGS. 15-17 showing partial retraction of the needle support after the cannula hub has been removed.

FIG. 18 illustrates the partially retracted structure of FIG. 17 after cannula hub 324 of catheter assembly 312 has been removed. Here the arms 396 are seen to be springing arms which spring outwardly away from front portion 358' a sufficient distance to release protrusions 400 from groove 410. Arms 396 are molded to normally spring open when they are not being pressed by cannula hub 324. In FIG. 18, the entire needle support 318' can be seen moving rearwardly within sleeve 314' in the retraction direction under the influence of the now partially compressed spring 316.

Figure 19:
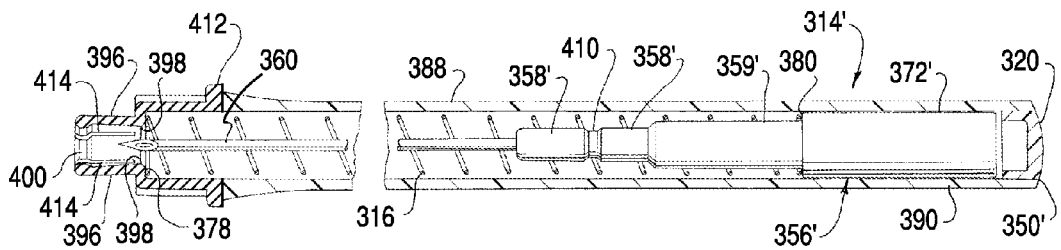
FIG. 19 is a partial cut away side elevation showing the embodiment of FIGS. 15-18 in the fully retracted position after the activation hub has been disconnected from the cannula hub.

FIG. 19 shows the completely retracted position of the structure of FIGS. 15-19. It is seen that sleeve 314' is long enough to receive the entirety of the retracted needle support 318' including the entirety of the needle 360 which is drawn in through the passageway 398 where it is no longer exposed.

Assembly of the components is from the rear. The spring can be inserted through the opening in the back of the sleeve and the needle support inserted preferably without the needle into the back of the spring which rests against stop 370. Then a plunger tool pushes against the back of the needle support as it is moved forward in the tube compressing the spring. The combination of the needle support being inside the spring in close support thereof and the spring being restrained by the sleeve prevents buckling of the spring during high speed installation. The sleeve acts as a guide for the spring. After the needle support is fully forward, it is held while needle 360 is glued in place. Then the needle is passed into the cannula and the cannula hub where the needle support is secured as described in various embodiments above. Once this is done, the tool is removed from the sleeve and end cap 320 is installed to retain the retracted parts after retraction. Although it is preferred that the needle be installed after the body is seated against the ledge in the activation hub, it is also possible to glue the needle in first, since the opening it must pass through is relatively large and slight curvature of the needle not likely to cause a "hang up" of the needle as it is moved forward.

As described above, embodiments of the present invention include retractable needle catheters using various manual and automatic retraction mechanisms. Embodiments of the present invention also contemplate a modular system and method of manufacturing in which catheters having either manually or automatic retraction can be manufactured using common parts. Further embodiments include a manually actuated retractable catheter and an automatically actuated retractable catheter in which all components are the same with the exception of the actuation hub. Yet further embodiments include a manually actuated retractable catheter and an automatically actuated retractable catheter in which all components are the same with the exception of a manual activation latch or button. Embodiments of a modular needle support 530 and modular activation hubs 510, 610, 710 used in such a system are shown in FIGS. 20-21.

Figure 21:
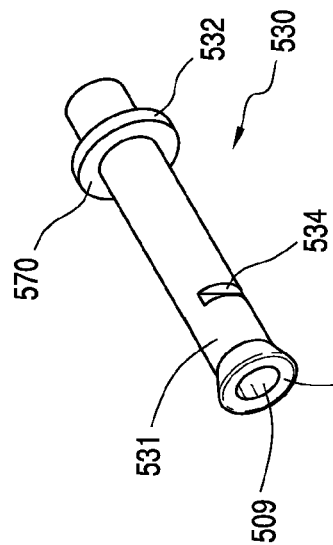
FIG. 21 is an isometric view of an embodiment of the needle support.

FIG. 21 illustrates an embodiment of a modular needle support 530 for use in such a system. The needle support has a needle receptacle 509 adapted to engage and secure a needle 550. Embodiments of the needle support incorporate features from both manually actuated and automatically actuated catheters described above. For example, embodiments of the needle support 530 include a generally cylindrical body 531. The forward end of the needle support may include an engaging element such as lip 520 or a similar extension that increases the diameter of the needle support beyond the diameter of the body 331. The needle support 531 may also include a second engaging element. For example in this embodiment, detent or notch 534, for receiving a keyed button 540, 640 and similar to the latch (40) described with respect to FIGS. 1-2, may be formed in the body 531. The notch 534 may be also be a slot or circumferential latch groove similar to the latch groove (34) shown in FIGS. 1-2.

Embodiments of the needle support 530 also comprise a stop section 532, which forms a stepped spring seat 570 extending radially outwardly from the body 531 at a rear portion of the needle support. This spring seat fits against a retraction member, such as a spring 561 that imparts a rearward bias to the needle support 530 in order to retract the needle once the keyed button 540, 640 has been actuated. The body 531 of needle support 530 has a diameter small enough to permit it to pass through an opening 523 of an activation hub, such as the hubs 510, 610, 710 illustrated in FIG. 20.

Figure 20:
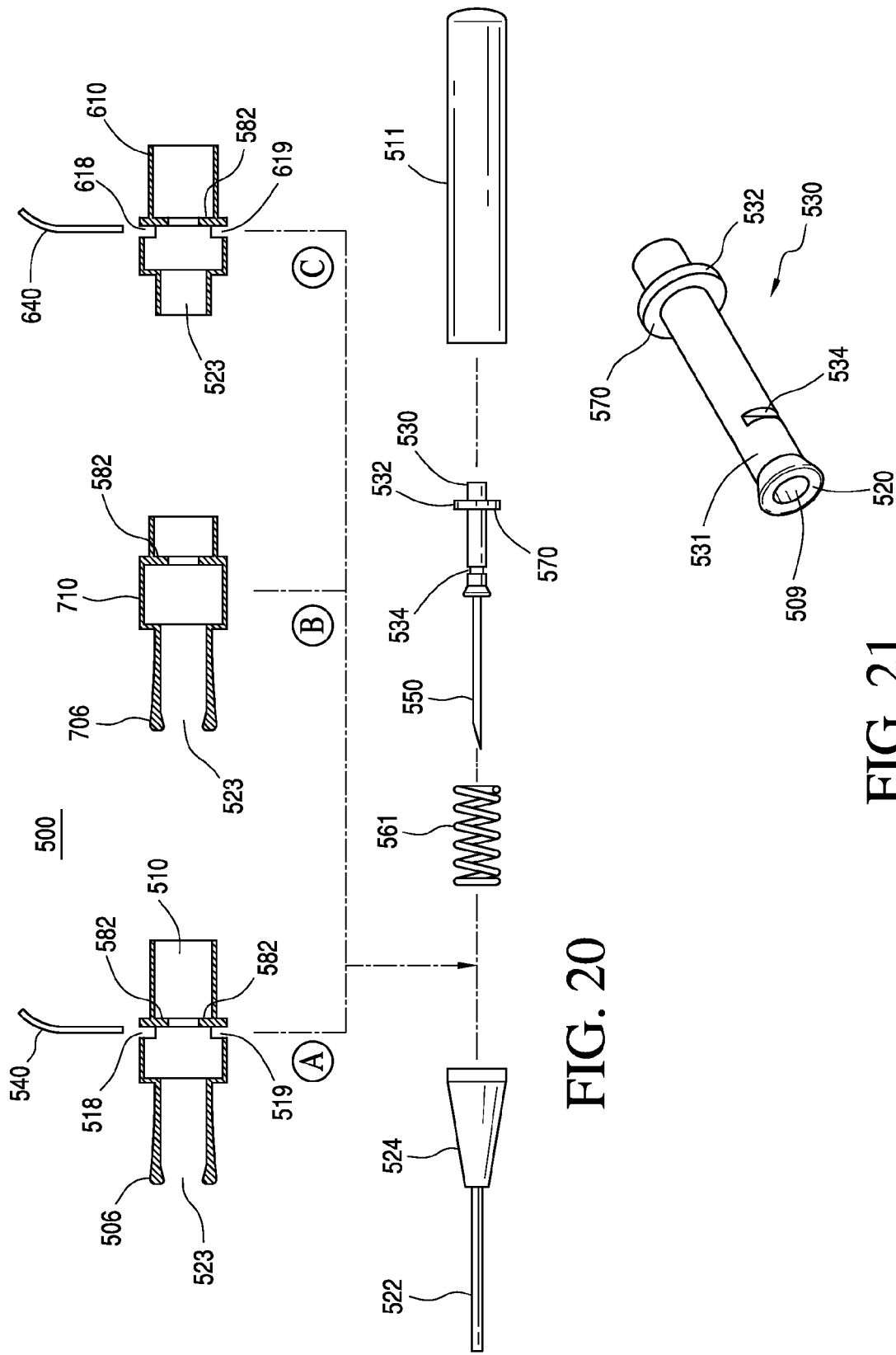
FIG. 20 is a schematic view showing various embodiments of a modular system of retractable needle catheters.

The schematic drawing in FIG. 20 illustrates a modular system 500 having three different optional activation hubs 510, 610, 710. Other components of the modular system, such as sleeve 511, cannula 522, cannula hub 524, needle 550, needle support 530 and spring 561 may be identical for each of the three options. Other common components may be used as illustrated by other embodiments described herein. Each of the optional hubs may have different features, or combinations of features, of manually actuated or automatically actuated activation hubs. However, each of the hubs 510, 610, 710 may be appropriately sized and configured so as to be interchangeable with the common elements of the catheter assembly.

For example, option "C" includes an activation hub 610 that includes features for manually actuated needle retraction. These features may be similar to those described with respect to FIGS. 1-2. Activation hub 610 includes a keyed button 640 and defines a slot 618 into which the keyed button 640 may be inserted. The keyed button 640 engages the notch 534 formed in the needle support 530. When the button 640 is manually actuated, the spring 561 causes the needle support 530 and needle 550 to retract within sleeve 511.

Option "B" in contrast includes features of for automatically actuated needle retraction. These features may be similar to those described with respect to FIGS. 3-10. Activation hub 710 comprises a plurality of engaging components 706. Each of the engaging components is separated from the adjacent components by a longitudinally-extending gap. Engaging components 706 form an opening 523 in a forward end of the activation hub 710. In an unassembled condition, the size of the opening is sufficient to allow the lip 520 of the needle support 530 to pass through the opening. However, once assembled, an inside surface of the cannula hub 524 urges the engaging components 706 toward each other to define an opening of reduced diameter. The reduced diameter is smaller than the diameter of the lip 520, and the engaging components secure the needle support 530 against retraction until the cannula hub is removed. At which point, the needle support 530 and needle 550 will automatically retract.

Figure 22:
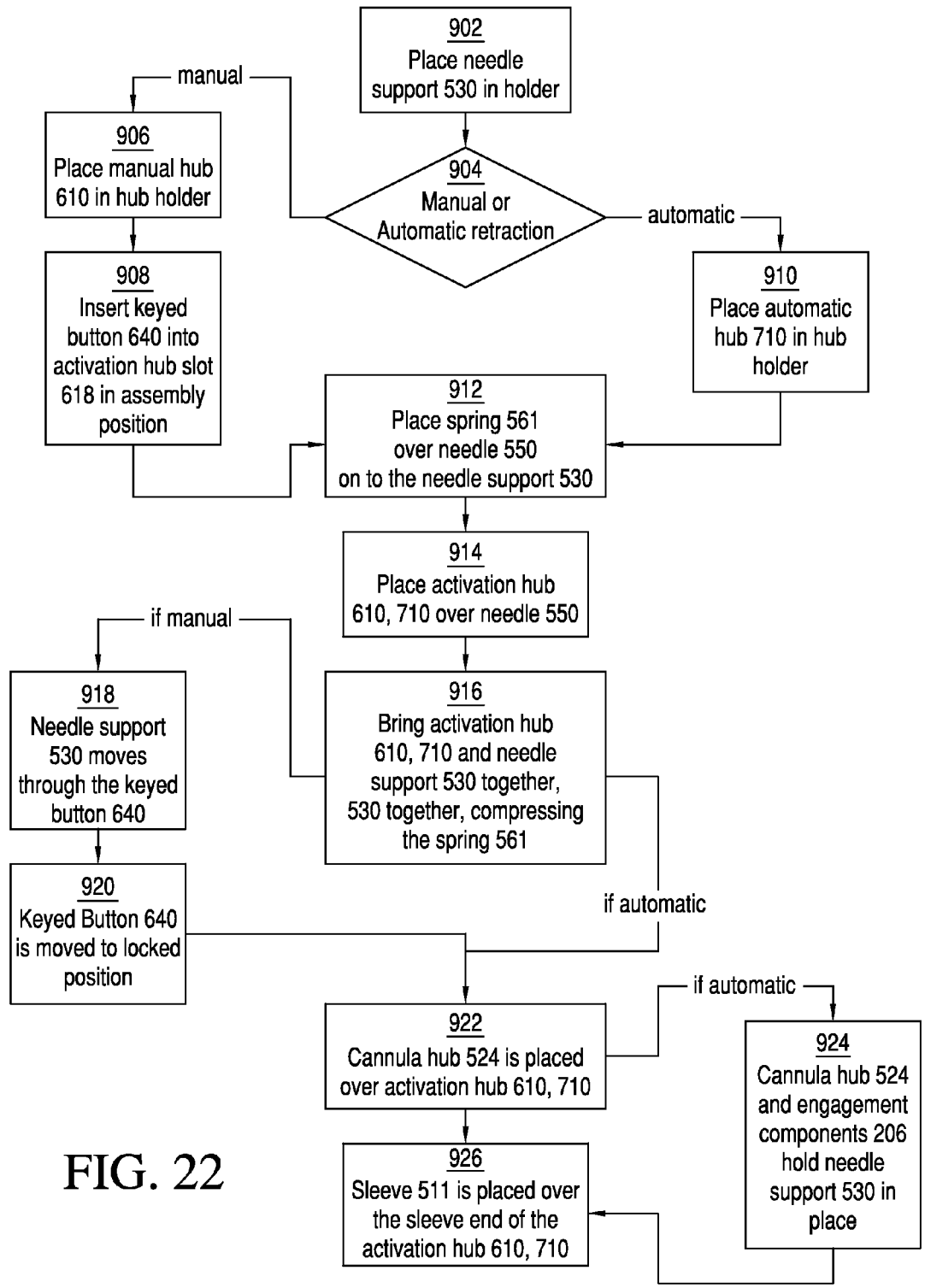
FIG. 22 is a flow chart of an embodiment a manufacturing process for the system of FIG. 20.

Accordingly, a manufacturing process in accordance with an embodiment of the present invention may be converted from manufacturing a manually retracting mechanism to manufacturing an automatically retracting mechanism by replacing only the activation hub. FIG. 22 shows a flow chart describing steps of an embodiment of a manufacturing process for alternatively assembling manually actuated or automatically actuated retractable needle mechanisms.

In a first step 902, the needle support 530 is placed in a manufacturing fixture, or holder. In the next step 904, the manufacturing process diverges depending on whether manual or automatic retraction is desired. If manufacturing a catheter with manual retraction, the process proceeds to step 906, which includes placing a manual hub 610 in a hub holder. In the following step 908, the keyed button 640 is inserted into the activation hub slot 618 in an assembly position. If manufacturing a catheter with automatic retraction, the process proceeds to step 910, which includes placing an automatic hub 710 in a hub holder.

The processes converge in step 912, which includes placing spring 561 over needle 550 on to the needle support 530. The spring rests on the spring seat 532 of the needle support 530. In the next step 914, the activation hub 610, 710 is placed over the needle 550. Next, in step 916, the activation hub 610, 710 and the needle support 530 are brought together, compressing the spring 561 between the spring seat 570 of the needle support and a spring seat 582 of the activation hub.

At this point, the processes diverge again. The process for manufacturing a manually retractable needle includes step 918, where the needle support 530 moves through the keyed button 640 to the point that the keyed button can engage the notch 534. In step 920, the keyed button is then moved to a locked position, engaging the notch 534 and thereby preventing the needle from retracting. In a process for manufacturing an automatically retracting needle catheter, the needle support 710 is not yet locked against movement due to the force of the spring 561 and the needle support must be held in place relative to the hub by manufacturing fixtures. Such manufacturing fixtures may include a spring holder inserted into the activation hub 710 to hold the hub 710 and needle support 530 together against the biasing force of the spring 561.

In step 922, which applies to both manually and automatically retracting mechanisms, cannula hub 524 is placed over the cannula facing end of the activation hub 610, 710. For the automatically actuated mechanism, in step 924, an inside surface of the cannula hub 524 engages the engaging components 706 that, in turn, engage the lip 520 of the needle support 530, securing the needle support against movement relative to the activation hub 710. At this point, step 926, the needle support holder can be removed and the sleeve 511 is attached to the rearward end of the activation hub 610, 710. This attachment may be accomplished by ultrasonic welding, adhesive, press fit or any other appropriate attachment means as would be apparent to one of ordinary skill in the art.

In an alternative embodiment, as illustrated by option "A" in FIG. 21, even greater commonality can be achieved by use of a combined activation hub 510. The combined hub includes features of both automatic activation hub 710 and manual activation hub 610. For example, combined hub 510 includes a slot 518 for engaging a keyed button 540 that generally corresponds to the design and functionality of slot 618 and keyed button 618 described above with respect to option "C."

In further embodiments of both option "A" and option "C" an activation slot 519, 619 may be incorporated into the activation hub 510, 610. The activation slot 519, 619 is formed in the activation hub opposite the keyed button slot 518, 618. The activation slot 519, 619 provides an opening in the hub to place a temporary latch (not shown). The temporary latch secures the needle support 530 from movement relative to the activation hub 510, 610 due to the biasing force of the spring 561. The temporary latch may engage notch 534 or some other notch, groove, or latching mechanism (not shown) in needle support 530. Accordingly button 540, 640 can be moved to and or maintained in the activated position during assembly of the device without triggering retraction of the needle 550. Or, for an automatically actuated device, the needle support 530 and activation hub 510 may be secured against movement until the cannula hub 524 is placed so as to secure the needle support in the extended position.

Alternatively, the activation slot 519, 619 provides an opening in the hub to place a temporary button insertion stop (not shown). The button insertion stop engages button 540, 640 and holds the button in the locked, or un-actuated, position. The button insertion stop thereby prevents the button from accidentally releasing the needle support 530 during insertion of the button in the assembly process, which would result in premature retraction of the needle.

Additionally, combined hub 510 includes engaging components 506 that generally correspond to the design and functionality of engaging components 706 described above with respect to option "B." In further embodiments, the combined hub 510 may be integrally formed with sleeve 11, further reducing the number of components.

Accordingly, with option "A", activation hub 510, it is possible to convert from manufacturing a manually retracting mechanism to manufacturing an automatically retracting mechanism by only including, or not, keyed button 540. If keyed button 540 is included during manufacture of the catheter assembly, the needle will only retract after the activation hub 510 has been removed from the cannula hub 524 and the keyed button has been manually actuated. Alternatively, if the keyed button is not included during manufacturing, the needle will automatically retract once the activation hub 510 has been removed from the cannula hub 524.

A cover, plug or other appropriate non-actuating piece may be attached to the activation hub 510 in place of the button 540 to preserve the look, feel or integrity of the catheter assembly. Button 540 has been described herein as a keyed button. However, this is not intended to limit the present invention to any specific type of button or activation mechanism, and the present invention contemplates the use of any manually actuated button, knob, grip or other activation mechanism as would be understood by one of ordinary skill in the art.

Figure 23:
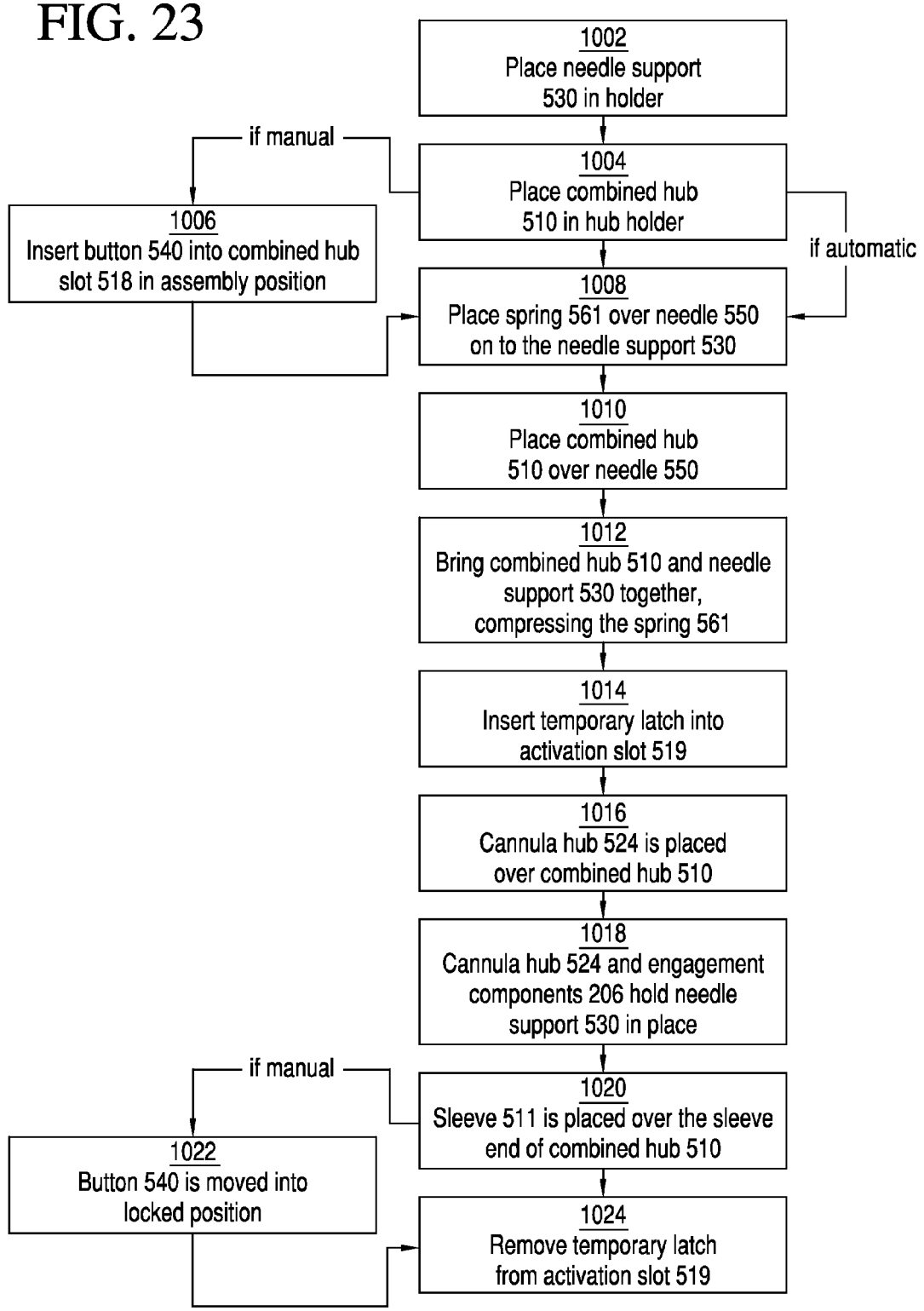
FIG. 23 is a flow chart of a further embodiment of a manufacturing process for the system of FIG. 20.

FIG. 23 shows a flow chart describing steps of a further embodiment of a manufacturing process for alternatively assembling manually actuated or automatically actuated retractable needle mechanisms.

In a first step 1002, the needle support 530 is placed in a manufacturing fixture, or holder. In the second step 1004, a combined hub 510 is placed in a hub holder.

In the next steps, the manufacturing process diverges depending on whether manual or automatic retraction is desired. If manufacturing a catheter with manual retraction, the process proceeds to step 1006, in which the button 540 is inserted into the combined hub slot 518 in an assembly position. If manufacturing a catheter with automatic retraction, the process proceeds to directly to step 1008.

The processes converge in step 1008, which includes placing spring 561 over needle 550 on to the needle support

530. The spring rests on the spring seat 532 of the needle support 530. In the next step 1010, the combined hub 510 is placed over the needle 550. Next, in step 1012, the combined hub 510 and the needle support 530 are brought together, compressing the spring 561 between the needle support and the activation hub.

At step 1014, a temporary latch is inserted into the activation slot 519 thereby preventing the needle from retracting. In step 1016, cannula hub 524 is placed over the cannula facing end of the combined hub 510. In the following step 1018, an inside surface of the cannula hub 524 engages the engaging components 506 that, in turn, engage the lip 520 of the needle support 530, securing the needle support against movement relative to the combined hub 510.

The sleeve 511 is then placed over the sleeve end of combined hub 511 in step 1020. In further embodiments, the combined hub 510 and sleeve 511 may be integrally formed and step 1020 would be unnecessary. In step 1022, the button 540 can now be moved into a locked position for manually retracting devices, and in step 1024, the temporary latch is removed from the activation slot 519.

The steps described herein and shown in FIGS. 22-23 are not intended to be exclusive. The steps described in the various embodiments may be interchanged, combined or deleted. In addition, there may be other necessary or desirable steps that form part of the manufacturing or assembly process as would be understood by one of ordinary skill in the art. The manufacturing and assembly process also contemplates the use of fixtures, holders, including vacuum holders, rotary dispensers and the like as appropriate.

The needle support 530 and activation hub 510, 610, 710 of the modular system 500 have been described a having certain exemplary features. However, it is contemplated that the needle support and activation hub may include any compatible features shown or describe with respect to other embodiments disclosed herein, including those shown in FIGS. 1-19, or other features as would be understood by one of ordinary skill in the art.

We claim:

1. A modular system of intravenous catheters comprising a catheter assembly:
   a cannula assembly including a cannula and a cannula hub;
   a needle;
   a sleeve defining an internal cavity with an opening at a front end of the sleeve;
   a needle support attached to the needle at a rear portion of the needle, the needle support slidably mounted within the internal cavity of the sleeve for movement of the needle from an extended position to a retracted position, the needle support comprising a first engaging element and a second engaging element; and
   a retractor that applies a force to the needle support biasing the needle support toward the retracted position; and
   an activation hub selected from the group consisting of a first activation hub and a second activation hub:
   wherein the first activation hub is connected to the front end of the sleeve and comprises a manually actuated release mechanism that engages the first engaging element of the needle support to secure the needle support against the biasing force of the retractor;
   wherein the second activation hub is connected to the front end of the sleeve and comprises an automatically actuated release mechanism that engages the second engaging element of the needle support to secure the needle support against the biasing force of the retractor; and
   wherein the first activation hub and the second activation hub are interchangeably selected.

2. The system of intravenous catheters of claim 1 wherein:
   the first activation hub comprises a button having a cutout;
   the needle support first engaging element comprises a detent; and
   the cutout of the button engages the detent.

3. The system of intravenous catheters of claim 2, wherein the detent is a circumferential groove.

4. The system of intravenous catheters of claim 2, wherein the detent is a groove that is recessed into a surface of the needle support.

5. The system of intravenous catheters of claim 1, wherein:
   the second activation hub comprises a resilient arm;
   the needle support second engaging element comprises a detent; and
   the resilient arm engages the detent.

6. The system of intravenous catheters of claim 5, wherein the detent is a lip extending outwardly from a surface of the needle support.

7. The system of intravenous catheters of claim 5, wherein the detent is a groove that is recessed into a surface of the needle support.

8. The system of intravenous catheters of claim 1, wherein:
   the first activation hub comprises a button having a cutout;
   the needle support first engaging element comprises a circumferential groove; and
   the cutout of the button engages the circumferential groove.

9. The system of intravenous catheters of claim 1, wherein the activation hub is selected from the group consisting of a first activation hub, a second activation hub, and a third activation hub;
   wherein the third activation hub comprises:
     a manually actuated release mechanism that engages the first engaging element of the needle support to secure the needle support against the biasing force of the retractor and
     an automatically actuated release mechanism that engages the second engaging element of the needle support to secure the needle support against the biasing force of the retractor; and
   wherein the first activation hub, the second activation hub, and the third activation hub are interchangeably selected.

10. The system of intravenous catheters of claim 9 wherein:
    the third activation hub comprises a button having a cutout;
    the needle support first engaging element comprises a first detent; and
    the cutout of the button engages the first detent.

11. The system of intravenous catheters of claim 10, wherein the first detent is a circumferential groove.

12. The system of intravenous catheters of claim 9, wherein:
    the third activation hub comprises a resilient arm;
    the needle support second engaging element comprises a second detent; and
    the resilient arm engages the second detent.

13. The system of intravenous catheters of claim 12, wherein the second detent is a lip extending outwardly from a surface of the needle support.

14. The system of intravenous catheters of claim 12, wherein the second detent is a groove that is recessed into a surface of the needle support.

15. The system of intravenous catheters of claim 9, wherein:
the third activation hub comprises a resilient arm and a button having a cutout;
the needle support first engaging element comprises a circumferential groove;
the needle support second engaging element comprises a lip extending outwardly from a surface of the needle support; and
the resilient arm engages the lip, and the cutout of the button engages the circumferential groove.

16. A modular system of intravenous catheters comprising:
a cannula assembly including a cannula and a cannula hub;
a needle;
a sleeve defining an internal cavity with an opening at a front end of the sleeve;
a needle support attached to the needle at a rear portion of the needle, the needle support slidably mounted within the internal cavity of the sleeve for movement of the needle from an extended position to a retracted position, the needle support comprising a first engaging element and a second engaging element;
a retractor that applies a force to the needle support biasing the needle support toward the retracted position; and
an activation hub connected to the front end of the sleeve, the activation hub selected from the group consisting of a first activation hub and a second activation hub;
wherein the first activation hub comprises a manually actuated release mechanism engaging the needle support first engaging element;
wherein the second activation hub comprises an automatically actuated release mechanism engaging the needle support second engaging element; and
wherein the first activation hub and the second activation hub are interchangeably selected.

17. The system of intravenous catheters of claim 16, wherein:
the manually actuated release mechanism comprises a button having a cutout, and the first engaging element comprises a notch formed in the needle support; and
the automatically actuated release mechanism comprises a resilient arm, and the second engaging element comprises a detent formed in the needle support.

18. The system of intravenous catheters of claim 16, wherein the activation hub is selected from the group consisting of a first activation hub, a second activation hub, and a third activation hub;
wherein the third activation hub comprises a manually actuated release and an automatically actuated release mechanism engaging the needle support second engaging element; and
wherein the first activation hub, the second activation hub, and the third activation hub are interchangeably selected.

* * * * *